US009795474B2

(12) United States Patent
Glick et al.

(10) Patent No.: US 9,795,474 B2
(45) Date of Patent: Oct. 24, 2017

(54) HYDROPHILIC IOL PACKAGING SYSTEM

(71) Applicants: Aaren Scientific, Inc., Ontario, CA (US); Carl Zeiss Meditec AG, Jena (DE)

(72) Inventors: Robert Glick, Trabuco Canyon, CA (US); Jürgen Zimmermann, Berlin (DE); Marco Müller, Berlin (DE)

(73) Assignees: CARL ZEISS MEDITEC AG, Jena (DE); AAREN SCIENTIFIC INC., Ontario, CA (US)

( * ) Notice: Subject to any disclaimer, the term of this patent is extended or adjusted under 35 U.S.C. 154(b) by 245 days.

(21) Appl. No.: 14/693,060

(22) Filed: Apr. 22, 2015

(65) Prior Publication Data

US 2015/0223931 A1     Aug. 13, 2015

Related U.S. Application Data

(63) Continuation-in-part of application No. 14/292,322, filed on May 30, 2014, now abandoned.

(60) Provisional application No. 61/895,184, filed on Oct. 24, 2013.

(51) Int. Cl.
*A61F 9/00* (2006.01)
*A61F 2/16* (2006.01)

(52) U.S. Cl.
CPC .................. *A61F 2/1691* (2013.01)

(58) Field of Classification Search
USPC ................. 206/438, 363, 370, 210, 5, 5.1, 6; 600/107; 53/425, 467
See application file for complete search history.

(56) References Cited

U.S. PATENT DOCUMENTS

| 4,860,885 A | 8/1989 | Kaufman et al. |
| 6,183,513 B1 | 2/2001 | Guenthner et al. |
| 7,954,636 B2 * | 6/2011 | Vincent-Aubry ..... A61F 2/1678 206/364 |
| 8,329,097 B1 | 12/2012 | Kunzler |
| 2004/0199174 A1 | 10/2004 | Herberger et al. |

(Continued)

FOREIGN PATENT DOCUMENTS

| EP | 1421917 A2 | 5/2004 |
| WO | 2006/102450 A2 | 9/2006 |
| WO | 2015-061401 A1 | 4/2015 |

OTHER PUBLICATIONS

European Patent Office, International Preliminary Report on Patentability (IPRP) issued in related International Application No. PCT/US2015/027130, dated Dec. 6, 2016 (7 pages).

(Continued)

*Primary Examiner* — Jacob K Ackun
(74) *Attorney, Agent, or Firm* — Cislo & Thomas, LLP

(57) ABSTRACT

A hydrophilic intraocular lens storage system includes: a) a substantially air tight container containing a small quantity of free water; and b) a foldable hydrophilic intraocular lens disposed within the container at a location wherein the lens is not immersed in liquid. The storage system can be employed to maintain the hydrophilic intraocular lens in a foldable state without being immersed in liquid. The method includes the step of storing the foldable intraocular lens within a substantially air tight package containing free water, the lens being stored within the package at a location wherein the lens is not immersed in liquid.

17 Claims, 4 Drawing Sheets

(56) References Cited

U.S. PATENT DOCUMENTS

| | | |
|---|---|---|
| 2007/0055370 A1 | 3/2007 | Sorochkin et al. |
| 2007/0250068 A1 | 10/2007 | Vincent-Aubry |
| 2008/0077237 A1 | 3/2008 | Isaacs et al. |
| 2008/0147082 A1* | 6/2008 | Pynson ............... A61F 2/1691 606/107 |
| 2009/0139879 A1* | 6/2009 | Tokarski ............. A45C 11/005 206/210 |
| 2009/0145091 A1* | 6/2009 | Connolly ............. B65B 25/008 53/467 |
| 2010/0036385 A1* | 2/2010 | Isaacs ............... A61M 37/0069 606/107 |
| 2011/0046634 A1* | 2/2011 | Rathert ............... A61F 2/1664 606/107 |
| 2011/0144654 A1 | 6/2011 | Isaacs et al. |
| 2011/0190777 A1 | 8/2011 | Hohl |
| 2012/0071888 A1* | 3/2012 | Putallaz ............... A61F 2/167 606/107 |
| 2012/0130390 A1 | 5/2012 | Davies et al. |
| 2012/0296424 A1 | 11/2012 | Bester |
| 2013/0226194 A1* | 8/2013 | Wanders ............... A61F 2/1667 606/107 |
| 2015/0297861 A1* | 10/2015 | Passalaqua ......... A61M 25/002 206/210 |
| 2016/0193081 A1* | 7/2016 | Gulati ................... A61F 2/167 53/425 |

OTHER PUBLICATIONS

International Preliminary Report on Patentability (IPRP) issued in related International Application No. PCT/US2014/061701, dated Apr. 26, 2016.

International Search Report and Written Opinion of International Application No. PCT/US14/61701, dated Dec. 31, 2014, 15 pages.

International Search Report and Written Opinion of International Application No. PCT/US2015/027130, dated Jul. 22, 2015, 12 pages.

* cited by examiner

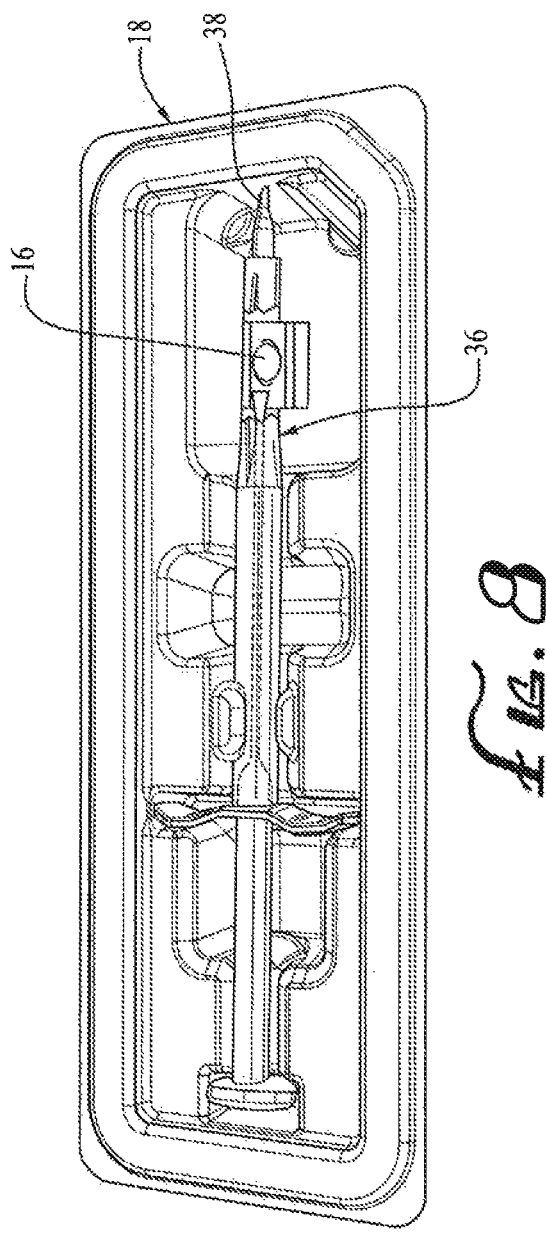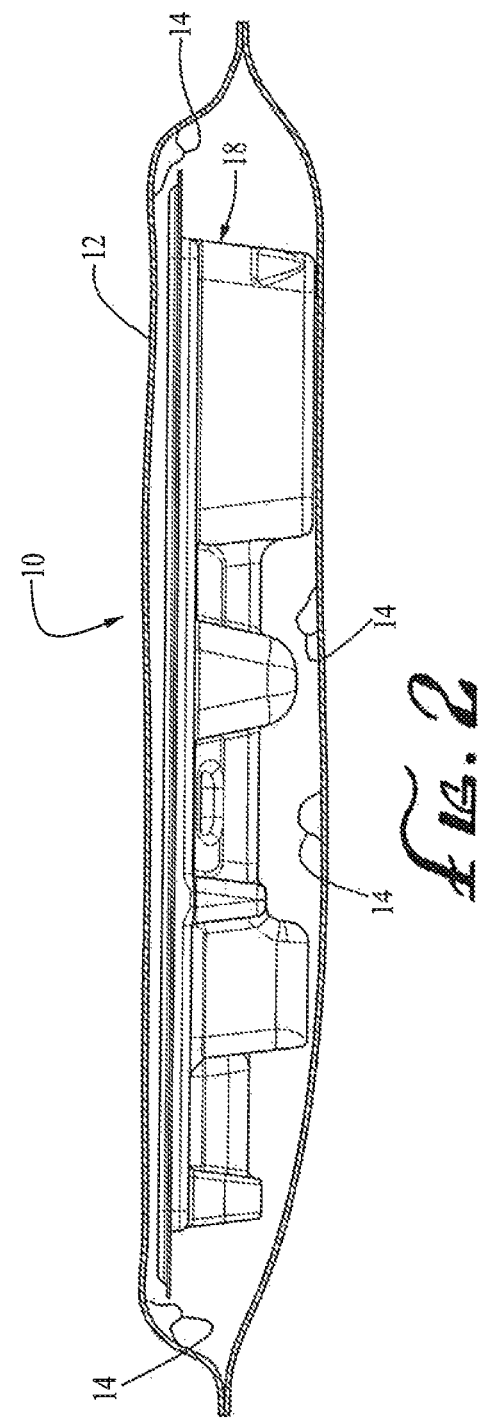

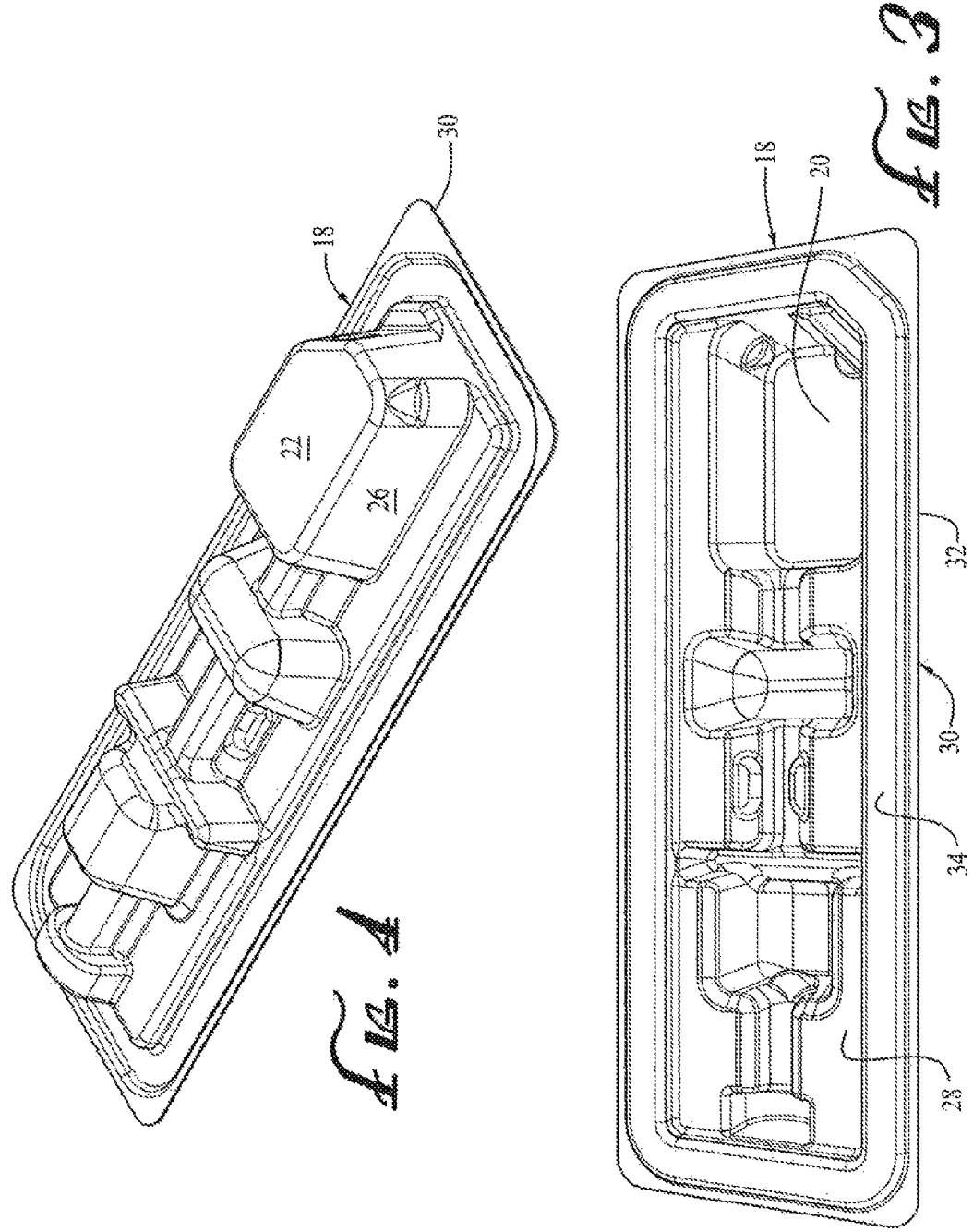

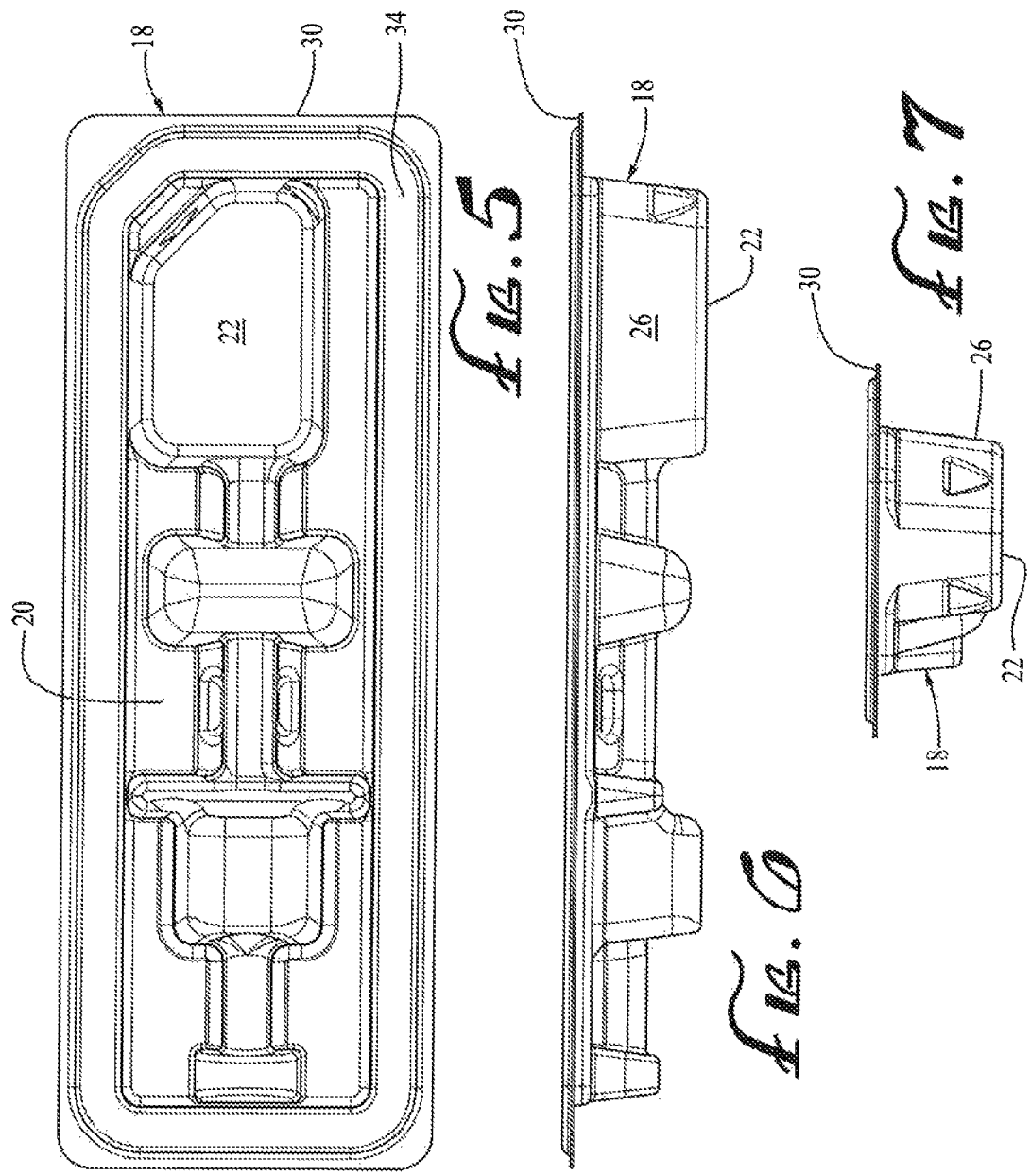

HYDROPHILIC IOL PACKAGING SYSTEM

RELATED APPLICATION

This application is a continuation-in-part of U.S. patent application Ser. No. 14/292,322 titled "HYDROPHILIC IOL PACKAGING SYSTEM," filed May 30, 2014, which claims priority from U.S. Patent Application Ser. No. 61/895,184, entitled "Hydrophilic IOL Packaging System," filed Oct. 24, 2013, the entireties of both of which are incorporated herein by reference.

FIELD OF THE INVENTION

This invention relates generally to packaging methods and systems, and more specifically to packaging methods and systems for foldable intraocular lenses.

BACKGROUND OF THE INVENTION intraocular lens polymers can be broadly categorized into two groups: (1) materials that absorb less than 1 percent water and (2) materials that absorb more than 1 percent water. Materials that absorb less than one percent water are typically referred to as hydrophobic polymers. Hydrophobic polymers may be foldable at room temperature. Their "foldability" results from their composition rather than from water acting as a plasticizer. Water absorbing polymers are typically referred to as hydrophilic polymers or hydrogels. The most, common materials in this group have approximately 25 percent water by weight. Hydrophilic polymers are usually foldable at room temperature by virtue of absorbed water acting as a plasticizer.

The conventional thinking in the intraocular lens industry is that hydrophilic intraocular lenses must be immersed in water or saline during storage to maintain a level of hydration needed for foldability at room temperature. Accordingly, lenses composed of these materials are almost ways packaged in normal saline (0.9 percent sodium chloride). Such lenses may reside in saline for up to five years prior to implantation. The normal saline in which these lenses are packaged is generally designed to mimic the conditions of the anterior segment of the eye where the lens will reside following implantation. This means that lenses will have similar dimension and mechanical characteristics in the eye as they have in the package where they reside prior to implantation.

Immersion in water or saline in the presence of other plastics needed for retention or insertion of the intraocular lens, however, can result in contamination of the intraocular lens by chemical entities contained in or produced by other plastic components in the packaging system. Being immersed in water or saline, the intraocular lens can "communicate" with plastic components via the liquid phase. Also, when an insertion instrument is removed from the package for use, water can flow from where the instrument was stored within the package to the intraocular lens.

The packaging of intraocular lens in water or saline has the additional disadvantage, especially when the intraocular lens is packaged with an insertion instrument, of increasing the weight of the package, thereby increasing shipping costs.

Moreover, implantation systems for hydrophilic intraocular lenses either require some kind of preparation of the injector or they use concepts of partly preloaded injector designs, e.g. with an adaptable cartridge with the preloaded intraocular lens including some preparation steps. All such preparation steps entail risks associated with possible false preparations or other mishandling by the surgeon or nurse. It is therefore advantageous to reduce the number of required preparation steps to as few as possible. This is especially true with so called MICS intraocular lenses—designed for micro incision cataract surgery. These lenses may require prefolding to facilitate advancement through the tubular region of the injector for better reproducibility of the injection process (with regard to tilting and rotation) and for proper folding of the intraocular lens.

SUMMARY OF THE INVENTION

The invention avoids the aforementioned problems in the prior art. In one aspect of the invention, the invention is a hydrophilic intraocular lens storage combination which comprises: a) a substantially air tight container containing a small quantity of free water; and b) a foldable hydrophilic intraocular lens disposed within the container at a location wherein the lens is not immersed in liquid.

In another aspect, the invention is a method of maintaining a hydrophilic intraocular lens in a foldable state without being immersed in liquid. The method comprises the step of storing a foldable intraocular lens within a substantially air tight package containing free water, the lens being stored within the package at a location wherein the lens is not immersed in liquid.

DRAWINGS

These and other features, aspects and advantages of the present invention will become better understood with reference to the following description, appended claims, and accompanying drawings where:

FIG. 2 is a cross-sectional side view of the combination of FIG. 1;

FIG. 3 is an upper side perspective view of a tray usable in the combination of FIG. 1;

FIG. 4 is a lower side perspective view of the tray illustrated in FIG. 3;

FIG. 5 is a bottom view of the tray illustrated in FIG. 3;

FIG. 6 is a side view of the tray illustrated in FIG. 3;

FIG. 7 is an end view of the tray illustrated in FIG. 3; and

FIG. 8 is a perspective top view of the tray illustrated in FIG. 3, showing retention of an intraocular lens and an intraocular lens injector.

DETAILED DESCRIPTION OF THE INVENTION

Figure 1:
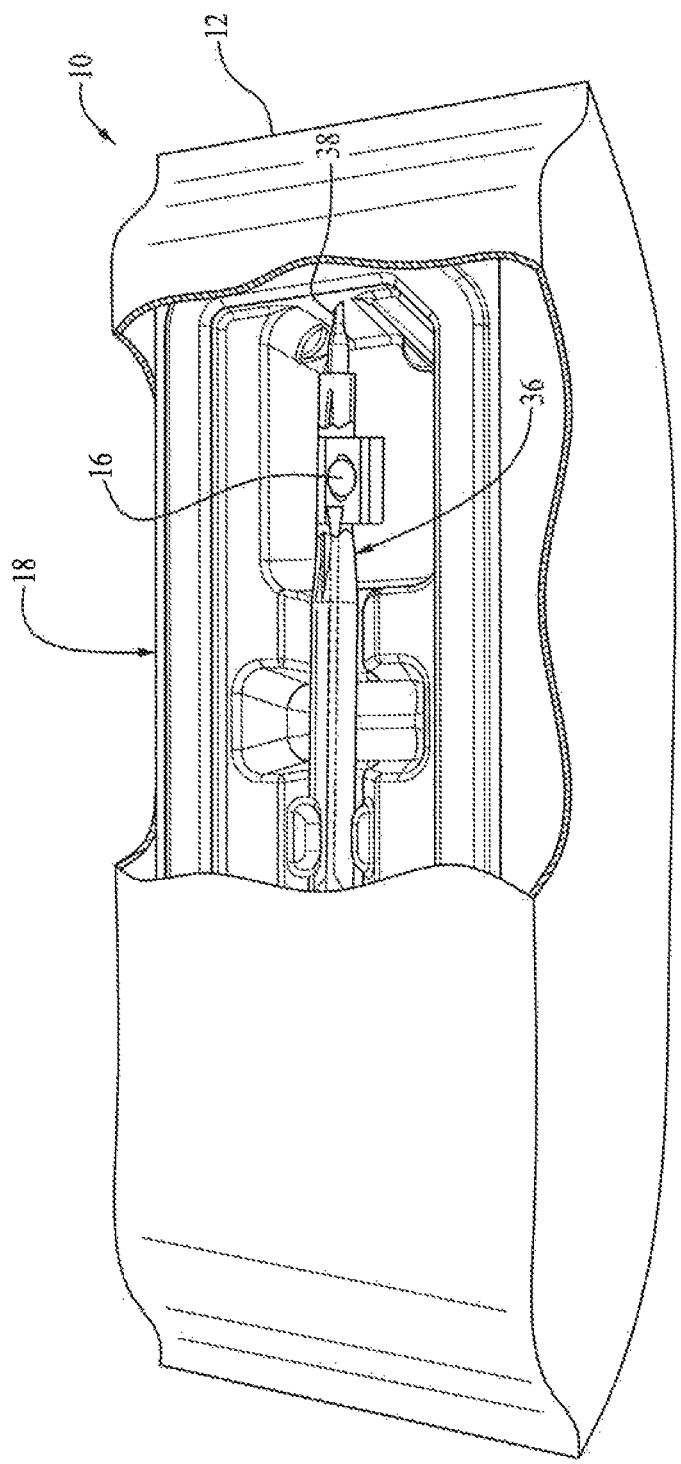
FIG. 1 is a partially cut away perspective view of a combination having features of the invention.

The following discussion describes in detail one embodiment of the invention and several variations of that embodiment. This discussion should not be construed, however, as limiting the invention to those particular embodiments. Practitioners skilled in the art will recognize numerous other embodiments as well.

Definitions

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers, ingredients or steps.

The Invention

In one aspect of the invention, the invention is a method of maintaining a hydrophilic intraocular lens in a foldable state without immersing the intraocular lens in liquid. The method comprises the step of storing the foldable intraocular lens within a substantially air tight container containing free water, the lens being stored within the container at a location wherein the lens is not immersed in liquid.

As used within this application, the phrase "free water" means water that is free to move about the interior of the air tight container and its contents; it may evaporate or condense or form drops; it is not bound to any matrix, substrate or absorbing substance; it is not primarily contained in a cavity or reservoir.

As used within this application, the word "water" means pure water, as well as any aqueous solutions which may contain salts or other solutes.

As used within this application, the word "foldable" means sufficiently pliable to allow the lens to be rolled into a cylinder with an external diameter sufficiently small to permit the lens to be injected into the eye of a patient through an injection tube having an external diameter of 2 mm or less.

The inventors have discovered the surprising fact that sufficient hydration of a hydrophilic intraocular lens can be maintained to the extent needed for folding and insertion into an eye without immersion of the lens in a liquid. In the invention, this is accomplished by packaging the lens with water saturated air, or nearly saturated air. By "nearly saturated" it is meant a humidity level of at least about 90%, preferably at least 95%. When saturated, such air cannot accept water from a hydrophilic intraocular lens, and when nearly saturated, such air can only accept a minimal amount of water from a hydrophilic intraocular lens. When the air within the container is nearly saturated and the volume of such air within the container is minimal (e.g. less than 100 cubic centimeters), the loss of water from the intraocular lens is unimportantly small.

Moreover, virtually any cycling of temperature within the sealed intraocular lens package during storage results in temperatures which fall below the package interior's dew point and which causes condensation upon the intraocular lens. Even small decreases in the package temperature may cause the air within the package to reach its dew point—thus resulting in condensation on all surfaces with the package, including on those of the intraocular lens. The presence of water droplets on the intraocular lens' surfaces assures a level of hydration adequate for foldability and delivery through a small diameter tube.

In a second aspect of the invention, the invention is a combination 10 comprising: (a) a substantially air tight container 12 containing free water 14; and (b) a foldable hydrophilic intraocular lens 16 disposed within the container 12 at a location wherein the lens 16 is not immersed in liquid. One embodiment of the combination 10 is illustrated in FIGS. 1 and 2.

As illustrated in FIGS. 1 and 2, the container 12 can be provided by a substantially air tight foil pouch. Other types of substantially air tight containers 12 can be used in the alternative. By "substantially air tight," it is meant that the container 12 is fully enclosed, but, perhaps, very small amounts of air may diffuse through the container walls.

In the embodiment illustrated in FIGS. 1 and 2, the intraocular lens 16 is stored securely within a tray 18. FIGS. 3-8 illustrate a typical tray 18 in detail. In FIGS. 3-8, the tray 18 has an elongate compartment 20 bounded by a bottom wall 22, side walls 26 and an elongate top opening 28. In one typical embodiment, the tray 18 can have a length of about 7.8 inches, a width of about 2.75 inches and a maximum depth of about 1.0 inch.

The tray 18 can be made from a thermoplastic, such as polypropylene. In the embodiment illustrated in FIGS. 3-8, the tray 18 can be made from 0.040" polypropylene.

In the embodiment illustrated in FIGS. 3-8, the tray 18 has a circumferential rim 30 with a raised outer lip 32 surrounding a recessed inner band 34. As illustrated in FIG. 2, the elongate top opening 28 is left unsealed.

The free water 14 is in an amount which barely exceeds that needed to moisture saturate the interior volume of the container 12 at temperatures up to those needed for steam sterilization, as well as to form small water droplets throughout the container 12. This amount of free water 14 should include that which would be lost over the storage duration due to diffusion through the walls of the container 12. The quantity of free water 14 within the container 12 depends on the volume of the container 12. For example, the quantity of (liquid) free water 14 within the container 12 is typically between about 0.1% and about 20% of the interior volume of the container 12. Typically, the amount of free water within the container will range between about 0.5 to about 5 milliliters, most typically between about 0.5 to about 3 milliliters, such as, for example, about 1 milliliter.

In all cases, the combination 10 is preferably autoclavable, that is, it is able to withstand being heated to 121 degrees C. or more for a period of half an hour or more.

Typically, a notice is appended to the exterior of the container 12 warning a user that the interior of the container 12 is moist.

As illustrated in FIGS. 1 and 8, the intraocular lens 16 can be disposed unfolded within an injector 36. The injector 36 is adapted to fold and inject the intraocular lens 16 into the eye of a patient through a cylindrical injection tube 38 having an external diameter sufficiently small to allow for surgical implanting of the lens 16 with minimum trauma to the eye. In a typical embodiment the cylindrical injection tube 38 has an external diameter of 2 millimeters or less.

In a typical method of assembling the combination 10, the injector 36 (loaded with the intraocular lens 16) is placed into the tray 18 and then the tray 18 is placed into the container 10. Before sealing the container 12, the desired amount of free water 14 is delivered (by adding droplets or by spraying) to the interior of the container 12, typically at random locations. Then the container 12 is sealed. During transportation and storage of the combination 10, the free water 14 typically clings in tiny droplets to the interior walls of the container 12 and to the exterior and interior of the tray 18—thereby providing sufficient humidity within the container 12 to maintain the intraocular lens 16 in a foldable state.

The invention greatly simplifies the manufacture and storage of hydrophilic intraocular lenses, reduces the costs of storage, reduces the cost of shipping and minimizes the risk of handling errors.

Having thus described the invention, it should be apparent that numerous structural modifications and adaptations may be resorted to without departing from the scope and fair meaning of the instant invention as set forth herein above and described herein below by the claims.

What is claimed is:

1. A method of maintaining a hydrophilic intraocular lens in a foldable state without immersing the intraocular lens in liquid, the method comprising the step of storing the foldable intraocular lens within a substantially air tight container containing free water, the lens being stored within the container at a location wherein the lens is not immersed in liquid.

2. The method of claim 1 wherein the quantity of free water within the container is between about 0.5 ml and about 5.0 ml.

3. The method of claim 1 wherein the container has an interior volume, and wherein the quantity of free water within the container is between about 0.1% and about 20% of the interior volume of the container.

4. The method of claim 1 comprising the additional step of heating the substantially air tight container containing the foldable intraocular lens and the free water to 121 degrees C. or more for a period of half an hour or more.

5. A combination comprising:
   a) a substantially air tight container containing free water; and
   b) a foldable hydrophilic intraocular lens disposed within the container at a location wherein the lens is not immersed in the water.

6. The combination of claim 5 wherein the quantity of free water within the container is between about 0.5 ml and about 5 ml.

7. The combination of claim 5 wherein the container has an interior volume, and wherein the quantity of free water within the container is between about 0.1% and about 20% of the interior volume of the container.

8. The combination of claim 5 wherein the combination containing the foldable intraocular lens and the free water is heated to 121 degrees C. or more for a period of half an hour or more.

9. A combination comprising:
   a) a substantially air tight container;
   b) between about 0.5 ml and about 5 ml free water disposed within the container; and
   c) a foldable hydrophilic intraocular lens disposed unfolded within an injector, the injector being adapted to fold and inject the intraocular lens into the eye of a patient through a cylindrical injection tube having an inside diameter of 2 mm or less.

10. The combination of claim 9 wherein the combination is heated to 121 degrees C. or more for a period of half an hour or more.

11. A method of maintaining a hydrophilic intraocular lens in a foldable state without immersing the intraocular lens in liquid, the method comprising the steps of:
   a) providing the combination of claim 5; and
   b) storing the foldable intraocular lens within the substantially air tight container containing free water, the lens being stored within the container at a location wherein the lens is not immersed in liquid.

12. The method of claim 11 wherein the quantity of free water within the container is between about 0.5 ml and about 5.0 ml.

13. The method of claim 11 wherein the container has an interior volume, and wherein the quantity of free water within the container is between about 0.1% and about 20% of the interior volume of the container.

14. The method of claim 11 comprising the additional step of heating the substantially air tight container containing the foldable intraocular lens and the free water to 121 degrees C. or more for a period of half an hour or more.

15. A method of maintaining a hydrophilic intraocular lens in a foldable state without immersing the intraocular lens in free water, the method comprising the steps of:
   a) providing the combination of claim 9; and
   b) storing the foldable intraocular lens within the substantially air tight container containing free water, the lens being stored within the container at a location wherein the lens is not immersed in free water.

16. The method of claim 15 wherein the container of step a) has an interior volume, and wherein the quantity of free water within the container is between about 0.1% and about 20% of the interior volume of the container.

17. The method of claim 15 comprising the additional step of heating the substantially air tight container containing the foldable intraocular lens and the free water to 121 degrees C. or more for a period of half an hour or more.

* * * * *